(12) United States Patent
Goldsborough (10) Patent No.: US 6,402,914 B1
(45) Date of Patent: Jun. 11, 2002

(54) IN-SITU LOADER FOR ELECTROPHORETIC GELS

(75) Inventor: Andrew Goldsborough, Nimes (FR)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/134,043

(22) Filed: Aug. 14, 1998

(51) Int. Cl.[7] .............................................. G01N 27/26
(52) U.S. Cl. ...................... 204/456; 204/618; 204/606; 204/466; 204/467; 204/616
(58) Field of Search ................. 204/456, 466, 204/467, 606, 616, 618, 619, 620; 422/100

(56) References Cited

U.S. PATENT DOCUMENTS

| | | | | |
|---|---|---|---|---|
| 4,431,506 A | * | 2/1984 | Gorman, Jr. et al. | 204/619 |
| 5,104,512 A | * | 4/1992 | Gombocz et al. | 204/607 |
| 5,217,591 A | * | 6/1993 | Gombocz et al. | 204/466 |
| 5,275,710 A | * | 1/1994 | Gombocz et al. | 204/461 |
| 5,736,025 A | * | 4/1998 | Smith et al. | 204/621 |
| 5,968,331 A | * | 10/1999 | Kambara et al. | 204/450 |

* cited by examiner

*Primary Examiner*—T. Tung
*Assistant Examiner*—Alex Noguerola
(74) *Attorney, Agent, or Firm*—Townsend and Townsend and Crew, LLP (57) ABSTRACT

The invention provides a novel "in situ" loader for electrophoretic gels. The loader comprises a body, containing at least one passage with an inlet and an outlet, and at least a part of the loader can be inserted into a gel holding portion of an electrophoresis apparatus. The loader can be loaded with samples, a variety of protocols performed without having to remove the samples, and electrophoresis performed directly from the loader into a gel. Centrifuges and PCR blocks adapted to accept the loader are also provided. The invention is particularly suited for use in automating DNA sequencing.

38 Claims, 5 Drawing Sheets

IN-SITU LOADER FOR ELECTROPHORETIC GELS

CROSS REFERENCE TO RELATED APPLICATIONS

Not applicable.

STATEMENT REGARDING FEDERALLY SPONSORED RESEARCH

Not applicable.

FIELD OF THE INVENTION

The present invention relates generally to devices for the electrophoretic separation of molecules. Specifically, the invention relates to an apparatus in which protocols can be performed and which can then load samples directly into gels for electrophoresis of molecules, and to equipment adapted to accept this apparatus.

BACKGROUND OF THE INVENTION

Electrophoresis is the process of separating molecules on the basis of the molecules' migrations in an electric field. In an electric field, a molecule will migrate towards the pole that carries a charge opposite to the charge carried by the molecule. Electrophoresis in a polymeric gel, such as an acrylamide or an agarose gel, stabilizes the electrophoretic system against convective disturbances. Further, the polymeric gel provides a porous passageway through which the molecules must travel. Since larger molecules will travel more slowly through the passageways than smaller molecules, use of a polymeric gel permits the separation by molecular size. The molecules can then be visualized by treatment with appropriate stains. If greater resolution is desired, the molecules can be radioactively labeled and the gel then exposed to X-ray film which, when developed, will reveal the migration position of the molecules.

Both vertical and horizontal assemblies are used in gel electrophoresis. In a vertical apparatus, sample wells are formed in the same plane as the gel and are loaded vertically. Horizontal gels are formed horizontally in a tray, with sample wells positioned in a vertical plane. The samples then electrophorese horizontally through the gel. Vertical gels are used particularly in analysis of proteins and in DNA sequencing, while horizontal gels are used for PCR analysis, including medical diagnostics, forensic comparisons and identifications, and preparative scale DNA purification and analytical work, for restriction enzyme digests, and for Northern blots.

Conventionally, when a vertical gel is to be formed, two glass plates are placed on top of each other, separated by a spacer on each side, and are positioned in a gel forming stand. A plastic or rubber "comb," so called because it has a number of teeth, or prongs, extending downward from its lower edge, is placed in the space between the plates at the top of the assembly, and a liquid, typically of polyacrylamide, is carefully poured into the space between the plates up to the lower edge of the comb. In vertical gels intended for electrophoresis of proteins, the gel is poured to cover the prongs of the comb. When the comb is removed, these prongs typically leave rectangular impressions, or "wells," in the edge of the gel. The gel is then covered with a standard "running buffer" solution, and samples to be electrophoresed, which have usually been centrifuged, and are often also subjected to heating steps, are mixed with a dense "loading solution" and then micropipetted, or drawn into and then injected from a fine gauge syringe, into the wells, a process known as "loading" the wells. The loading solution usually also contains a dye so that the technician loading the wells can confirm visually the placement of the sample into the correct well.

In DNA sequencing, the procedure is slightly different. DNA sequencing typically employs a "shark's-tooth" comb, which when seen from the front has a flat top and a bottom with prongs shaped like upside-down triangles. The comb is placed in the top of the gel forming apparatus between the glass plates, with the flat side down, and the gel poured. When the gel has set, the comb is removed, to expose the flat surface of the gel and the comb is inverted so that the teeth point down. The comb is then lowered so that the teeth just touch the surface of the gel, with a triangular space open between the teeth, the top of which extends beyond the glass plates of the apparatus. The samples are then loaded through the open spaces between the teeth and run down the interior sides of the glass plates to sit on the flat surface of the gel, separated from each other by the teeth. Gels used for DNA sequencing, in particular, are typically quite thin (between 0.2 and 0.4 mm), requiring considerable care in handling and sample loading.

Horizontal gels are typically formed of liquid agarose poured into a tray, and a comb is positioned to hang into the agarose from above. Once the gel has set, the comb is removed, leaving wells formed by the prongs of the comb. Samples to be electrophoresed are again mixed with a dense "loading solution" to reduce loss of the sample into the running buffer, and are loaded into the wells by a pipette or from a syringe. The electrophoresis of both vertical and horizontal gels is well known in the art and is set forth in, e.g., Sambrook et al., *Molecular Cloning, A Laboratory Manual* (2nd Ed. 1989) Cold Spring Harbor Laboratory, Cold Spring Harbor, N.Y.; and Harlow and Lane, *Antibodies, A Laboratory Manual* (1988), Cold Spring Harbor Laboratory, Cold Spring Harbor, N.Y.

Recently, the use of electrophoresis has undergone explosive growth. The Human Genome Project, which has undertaken to sequence the entire human genome, for example, currently consumes the efforts of a large number of laboratories, and programs are also underway to determine the complete DNA sequence of important pathogens and other organisms, including a number of plants. The use of DNA comparisons in forensic work and in medical diagnostics has also been increasing rapidly.

The high volume of DNA sequencing and other forms of electrophoresis has led to attempts to automate the process. One bottleneck in the efforts to automate electrophoresis in general, and DNA sequencing in particular, has been loading the samples in the wells. While automated equipment has been able to take over much of the repetitive work involved in preparing samples for electrophoresis, it has proven difficult to build equipment capable of loading individual wells, and especially hard to build equipment capable of loading a well in the space (only 0.2 to 0.4 mm) between the plates of a typical DNA sequencing gel. Thus, technicians load the bulk of these gels by hand.

Manual loading is generally undesirable, especially for high volume work such as sequencing. Not only does it slow the process, but it also introduces the chance for error in the order of the samples as the technician repetitively transfers sample after sample from tubes or microtiter plates to the wells. Further, manual loading increases the risk that the technician will be exposed to biohazards, or to radioactivity from radiolabeled samples. It also increases the risk of contamination of the samples due to handling errors such as a failure to change a pipette tip between samples.

Finally, the multiple transfers of samples between containers, such as centrifuge tubes and microtiter plates, and finally into the wells of a gel, are themselves undesirable. Macromolecules, which are the molecules to which electrophoresis is most often applied, are particularly susceptible to cleavage from shearing forces, which are created each time they are pipetted or transferred by syringe from one container to another. Therefore, the current multiple transfers of samples to and from microtiter plates and centrifuge tubes and finally into the wells of electrophoresis gels can alter or destroy the very molecules whose detection is sought.

Accordingly, a need exists in the art for a means of loading gels which is more amenable to automation. Further, a need exists for a means of loading gels which reduces the opportunity to alter the order of samples, reduces the exposure of lab workers to potential hazards, and reduces the number of times a particular sample has to be transferred between containers. The subject invention fills these and other needs.

SUMMARY OF THE INVENTION

The invention provides an "in situ" loader for electrophoresis gels, comprising a body which includes at least one passage. The passage contains an inlet and an outlet, which are spaced along the passage in fluid communication. At least a part of the loader is of a dimension which permits insertion of that part of the loader into a gel holding portion of an electrophoresis apparatus.

Further, at least a portion of the bore or hollow of the passage can be enlarged, to define a reaction chamber. The passage can have a barrier located in the interior of the passage to prevent any macromolecules located in the passage, and particularly in the reaction chamber, from flowing to the outlet under normal gravity. The internal barrier will typically be located below (often immediately below) the reaction chamber.

The loader can contain one or more than one passages. The outlet or outlets of the passage can define a flat edge. The loader can be made of a material which has a low affinity for nucleic acids, for proteins, or for both.

The loader can further comprise a barrier inside or at the outlet, wherein the barrier is a permeable membrane. The permeable membrane can be covered, externally to the outlet, with a removable impermeable material. The removable impermeable material can be bonded, or thermally bonded, to the loader. The removable impermeable material can be a metal foil, a plastic film, or a metallized film. The outlet can also be covered by a removable metal, plastic, or rubber sleeve, or one made of another material inert to the reagents to be used which is capable of being fitted snugly to the loader and of withstanding the procedures to be employed in connection with the loader in question.

The barrier at the outlet can also be moveable or removable.

The loader can also have a section which is larger, typically in the thickness, than the portion of the loader intended for insertion into the gel electrophoresis or gel forming apparatus. The loader can transfer heat to and from the contents of the loader at a rate suitable for conducting the polymerase chain reaction. The passages of the loader can contain an electrode or electrical contact permitting direct access to electric current. A side of the loader other than the side through the molecules are intended to undergo electrophoresis may be made in whole or part of metal or of another material which conducts electricity, to permit current to reach a sample in the interior of a passage.

The loader can have outlets which are spaced more closely than are the corresponding inlets. Two or more passages of the loader can have not only individual inlets providing access to the respective individual passage, but also an additional, common inlet providing access to each of the passages in connection with the common inlet. One or more passages, or wells, of the loader can also be preloaded with one or more reagents.

The invention also provides a system comprising an "in situ" loader for electrophoretic gels comprising a body with at least one passage defined therein, the passage including an inlet and an outlet, wherein the inlet and the outlet are spaced along the passage in fluid communication, and further wherein at least a part of the loader is of a dimension which permits insertion of that part of the loader into a gel holding portion of an electrophoresis apparatus, and a gel.

Further, the invention provides a method for separating macromolecules electrophoretically using a gel, wherein the macromolecules are loaded into a loader having an inlet in fluid communication with a hollow passage in fluid communication with an outlet, the macromolecules being drawn through said outlet into a gel upon application of an electric current.

The invention further provides a kit comprising "in situ" loader for electrophoretic gels comprising a body with at least one passage defined therein, the passage including an inlet and an outlet, wherein the inlet and the outlet are spaced along the passage in fluid communication, and further wherein at least a part of the loader is of a dimension which permits insertion of that part of the loader into a gel holding portion of an electrophoresis apparatus, and a gel electrophoresis apparatus.

Further, the invention provides a centrifuge adapted to hold a loader as set forth above, and a system comprising such a centrifuge and such a loader. The centrifuge may have means to heat or to cool samples, or to do both.

Finally, the invention provides devices for performing PCR, adapted to hold a loader as described above.

BRIEF DESCRIPTION OF THE DRAWINGS

FIG. 3 shows side views of horizontal gel loaders.

FIG. 4a shows the arrangement of the internal barrier. FIG. 4b shows the barrier capturing a molecule of interest during centrifugation. FIG. 4c shows the addition of dye and buffer. FIG. 4d shows the loader in position in a gel electrophoresis apparatus, immersed in buffer. FIG. 4e shows the loader in position during electrophoresis (indicated by the charge symbol in the lower right corner of the figure), with the molecule of interest having been drawn over the internal barrier and in the process of entering the gel.

DETAILED DESCRIPTION OF THE INVENTION

I. INTRODUCTION

The invention provides a novel apparatus for loading samples into electrophoresis gels.

The invention provides a gel loader, or "comb," 10 into which the samples can be loaded prior to formation of a gel. Samples loaded into the loader can be electrophoresed directly from the loader into the gel, with the loader remaining in place, or "in situ," during the electrophoresis.

The gel loader has a number of advantages over conventional gel loading methods. In some embodiments, reactions, and even whole protocols, such as PCR and restriction enzyme digests, can be performed in the loader prior to electrophoresis. This reduces the number of times that the samples need to be handled and the number of times the samples need to be micropipetted in and out of containers prior to being loaded into the wells of a gel. This reduces the risk that a technician may be exposed to biohazards or to radioactivity, reduces the possibility that samples will be contaminated, and reduces the possibility that samples will be damaged or destroyed by shearing forces by multiple transfers between containers. Since the loader reduces the number of transfers, and maintains the samples in invariant order once loaded, it also reduces the possibility that a technician will inadvertently change the order of the samples during the multiple transfers currently required. Further, since the walls of the passages of the loader hold the samples in place and, in horizontal gels, constrains samples from being washed over the top of the well by the running buffer, the loader also reduces or eliminates the need to mix the samples with chemicals extraneous to the electrophoresis but needed in conventional electrophoresis setups, such as dyes and loading solutions.

Finally, because the loader can be made with inlets larger than the dimensions of the gel into which the samples are to be electrophoresed, the loader is much easier to use in automated systems than are the wells created by traditional means of gel loading. This permits a considerable increase in the speed with which DNA sequencing, in particular, can be accomplished. Accordingly, the gel loader provides a significant advance in the technology of performing electrophoretic separations of nucleic acids, proteins, and other molecules.

II. DEFINITIONS

The terms "gel loader," "loader," and "comb" are used interchangeably herein except in those few instances, carefully indicated, where the word "comb" refers to the traditional solid "comb" used to form wells when electrophoresis gels are poured, rather then the gel loading "comb" of the invention.

The terms "vertical gel loader" and "vertical loader" 10 mean a loader designed for use with a gel used in a vertical orientation. The terms "horizontal gel loader" and "horizontal loader" 30 mean a loader designed for use with a gel used in a horizontal orientation.

As used herein, "passage" 12 refers to a hollow channel or duct 18 traversing a portion of a gel loader, and connecting an inlet 14 in the gel loader to an outlet 16. The outlet 16 may be covered by a permeable membrane permissive of electrophoresis through the membrane, or by a movable or removable cover until at or about the time the loader is placed in contact with a gel prior to initiating electrophoresis. Typically, the inlet 14 will be located in the top portion of the loader and the outlet will be disposed some distance away. Generally, the outlet will be located below the inlet so that macromolecules placed in the inlet are assisted by gravity in reaching the outlet. In some embodiments, loaders are provided which have common inlets 20, that is, a single inlet with channels 22 connecting it to more than one outlet. In loaders intended for use with gels to be run in a vertical direction, the outlet of the passage will typically be located at the bottom edge of the loader. In loaders intended for use with gels to be run in a horizontal direction, the outlet 30 will generally be along the wall of the loader and may constitute all or only a portion of the wall.

A "common inlet" 20 is an inlet in fluid connection to more than one passage, or well.

The term "reaction chamber" 40 refers to a section of the passage which, in vertical gel loaders, is enlarged in bore, capacity or size relative to the rest of the passage (particularly that portion of the passage near the outlet), providing a space for reactions, such as the interaction of primers, nucleotides, and nucleic acids in the polymerase chain reaction, to take place in the body of the gel loader. As shown in FIG. 3, in horizontal gel loaders, all or a portion of the bore of the lower section of the passage can serve as a reaction chamber, since the lower section of the loader does not have to fit into as confined a space as does the lower portion of a vertical loader.

Except as otherwise noted, the terms "passage," "well," and "prong" are used interchangeably, and refer to the hollow channel in a gel loader through which samples to undergo electrophoresis are conducted from the inlet to the outlet and from which the samples can enter a gel. In loaders with common inlets, the common inlet has an additional hollow channel providing fluid connection to more than one passage or well. In a few, clearly indicated instances, the term "prong" refers to the more traditional, solid prong of a solid "comb" which forms a well when an electrophoresis gel is poured around it.

The "lanes" of a gel are the portions of the gel through which the molecules loaded onto the gel travel when subjected to electrophoresis.

As used herein, "sample" means a nucleic acid, protein, or other molecule intended for electrophoretic separation, with or without first undergoing one or more procedures, such as PCR or restriction enzyme digestion. The "sample" can therefore be, for example, a nucleic acid which is subjected, in the loader, to restriction enzyme digestion, with the resulting fragments separated by electrophoresis, or a nucleic acid which undergoes PCR in the loader, before the loader is placed in contact with a gel and electrophoresis conducted. The nucleic acid, protein or other molecule will usually be in a buffer or other liquid to facilitate handling, electrophoresis, and the like.

"Loading" and "to load" mean the process of placing reagents or samples in a well of a gel loader or, in connection with conventionally made gels, of placing reagents or samples in the wells of a gel.

Conducting electrophoresis of a sample in a gel is commonly referred to in the art as "running" the gel.

As used herein, "reagent" refers to any chemical or substance, reactive or non-reactive, which may be desired to be used with respect to a particular protocol or procedure.

III. STRUCTURE AND COMPONENTS OF A GEL LOADER OF THE INVENTION

1. Shape of the Gel Loader a). Introduction

Figure 1:
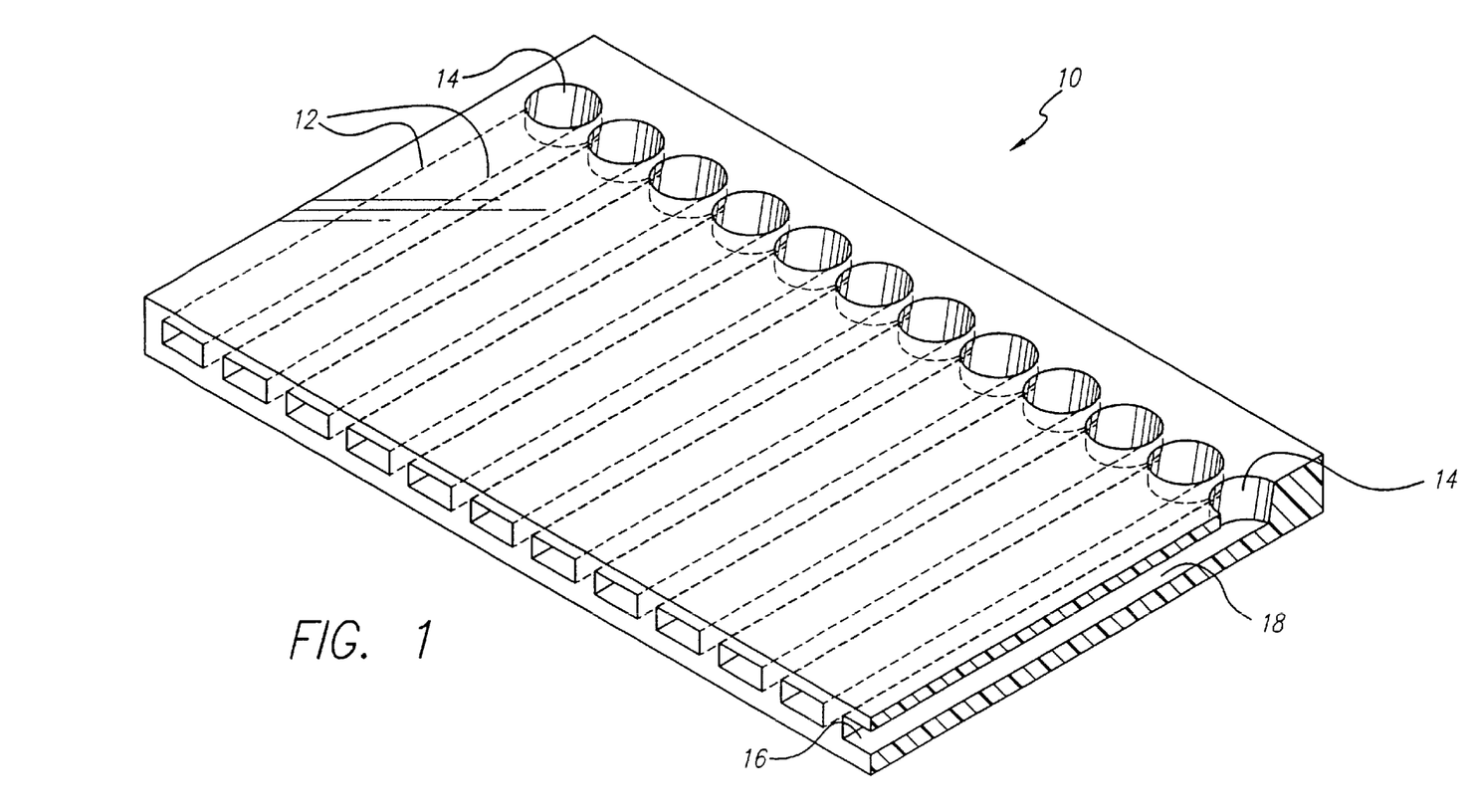
FIG. 1 is a perspective view showing a typical arrangement of inlets, outlets, and passages for a vertical gel loader with 12 wells.
Figure 2:
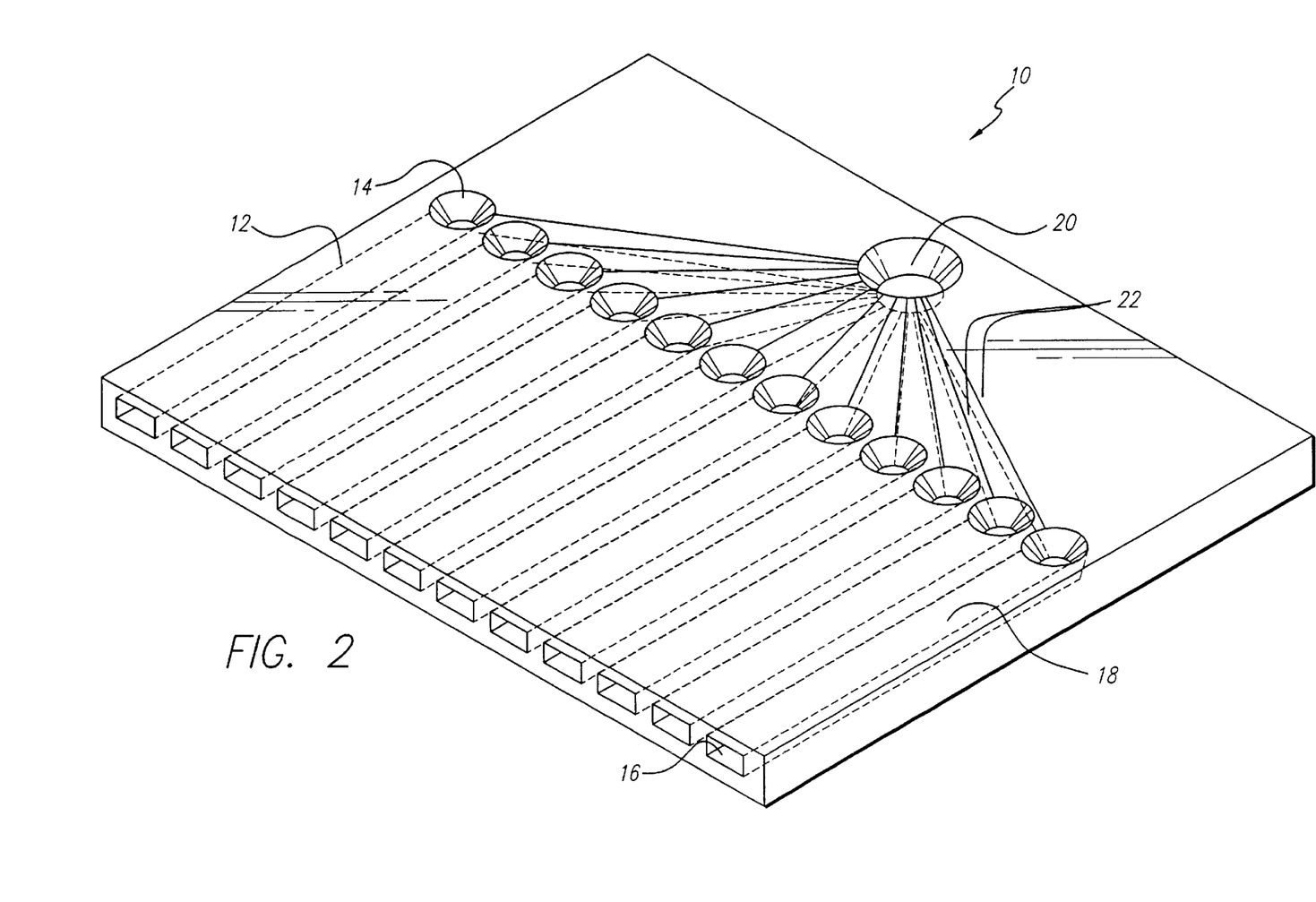
FIG. 2 is a perspective view showing a typical arrangement of inlets, outlets and passages for a vertical gel loader with 12 wells which have both an individual inlet and a shared, common inlet.
Figure 4:
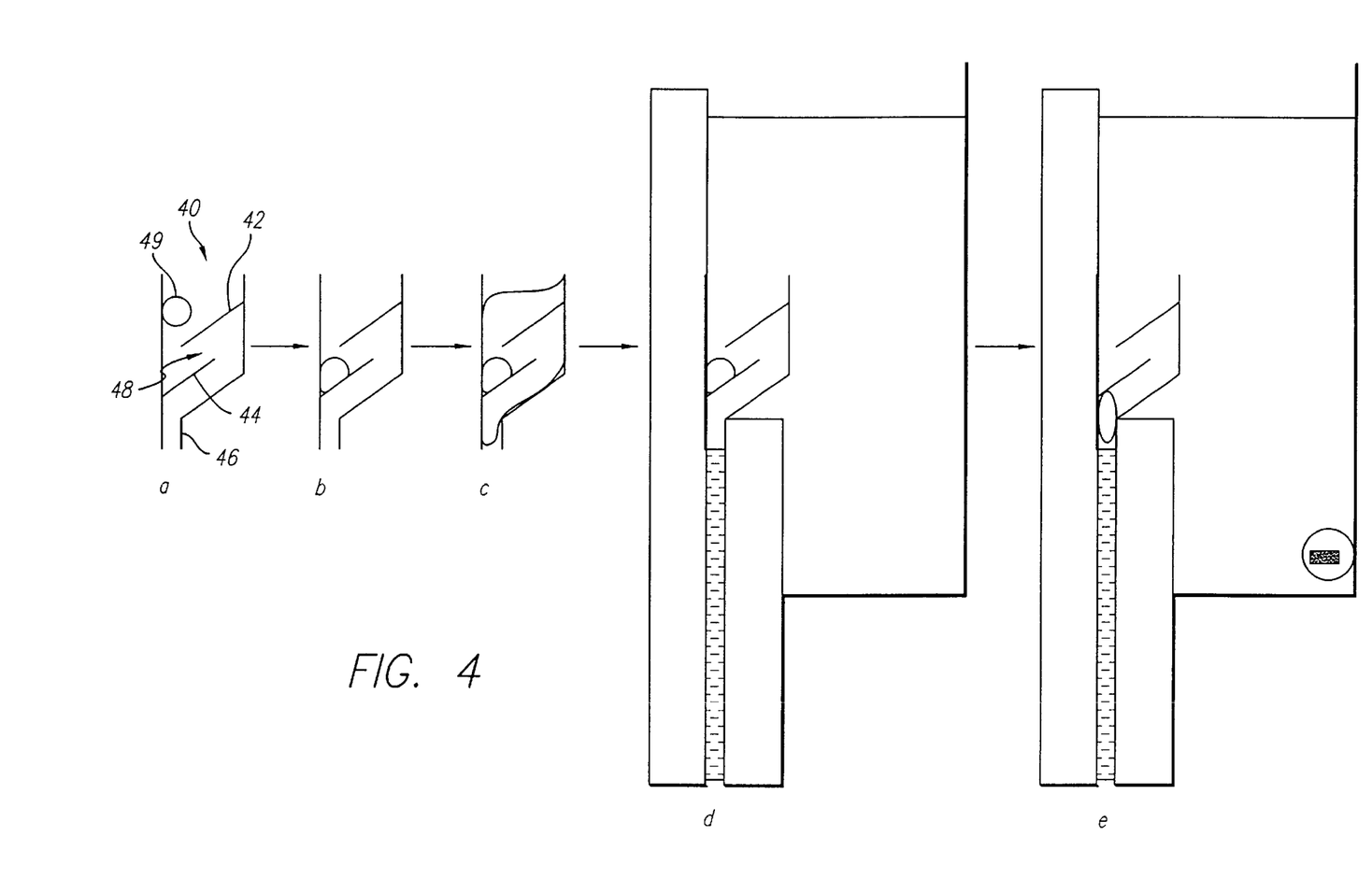
FIG. 4 shows side views of a vertical gel loader with an internal barrier.
Figure 5:
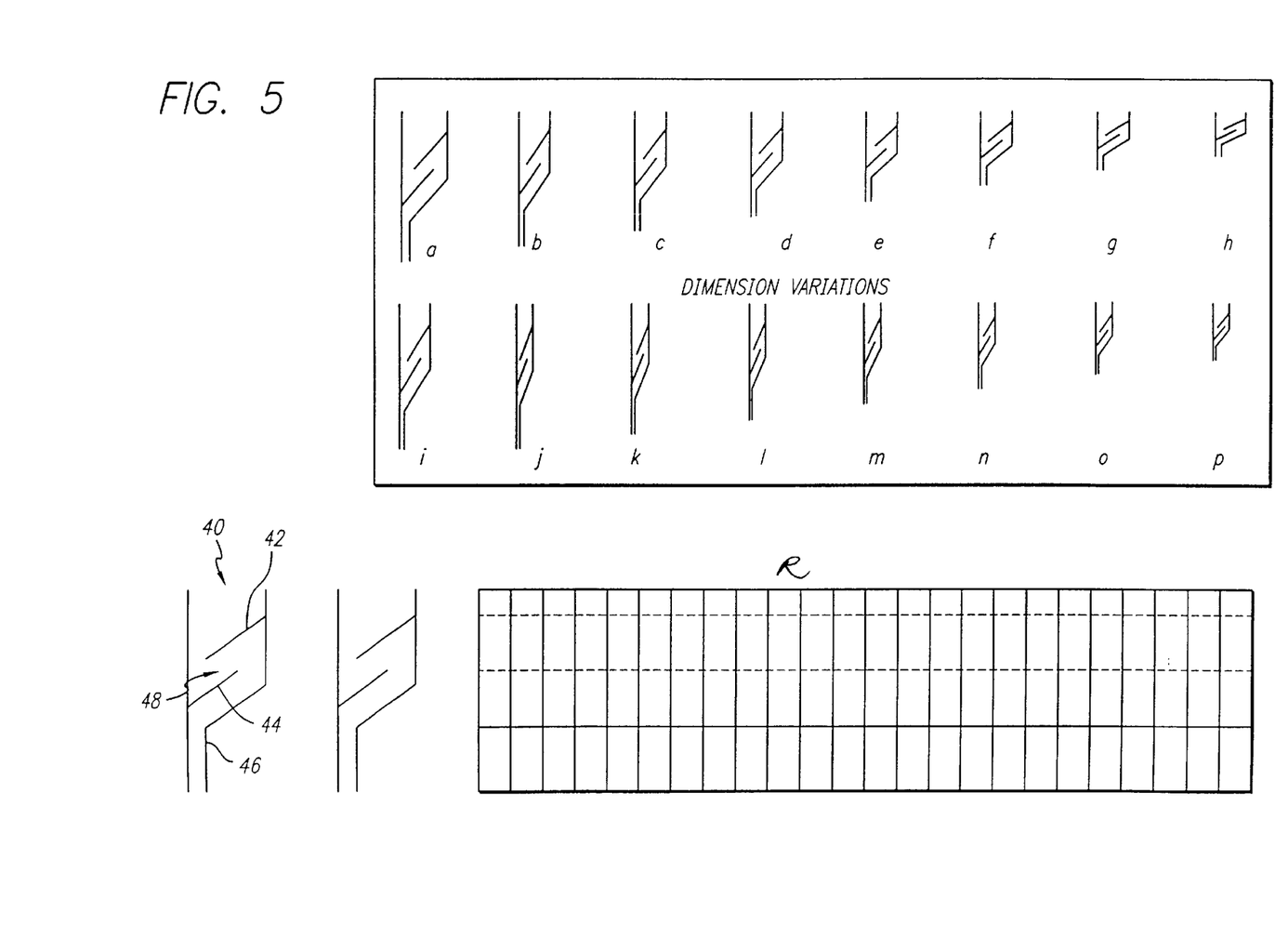
FIG. 5 shows dimensional variations in vertical gel loaders with internal barriers.

As shown in FIG. 1, a gel loader of the invention comprises a body 10 containing one or more passages or wells 12 for loading a lane of a gel, with an inlet 14 located in the top portion of the loader, an outlet 16 in the bottom portion, and a hollow channel 18 connecting the inlet and the outlet (for ease of illustration, the body 10 has been made somewhat longer and the sides somewhat thicker than would be typically be the case in practice). In the particular embodiment of the invention shown in FIG. 1, the inlets 14 are positioned below the top of the device and have a beveled edge to facilitate introducing reagents and samples into the passage by, for example, a pipette or syringe. The connection of the inlet to the passage may also, for example, be angled upwardly, to permit a pipette or syringe to load the well from a more vertical orientation. In other embodiments, the inlet or inlets 14 can be positioned in, at or along the top, or the top edge of the device, as shown in FIGS. 4 and 5. FIG. 2 shows a loader of the invention in which each of the wells has an individual inlet 14, and also has a second inlet 20, which has channels 22 on the interior of the loader connecting this "common inlet" 20 to, in this embodiment, each of the individual wells 12 on the loader so that reagents introduced through inlet 20 are delivered to all of the wells at the same time. As discussed below, the design of the loader will also vary somewhat depending on the orientation of the gel and the thickness of the gel with which the loader is intended to be used.

Figure 3A:
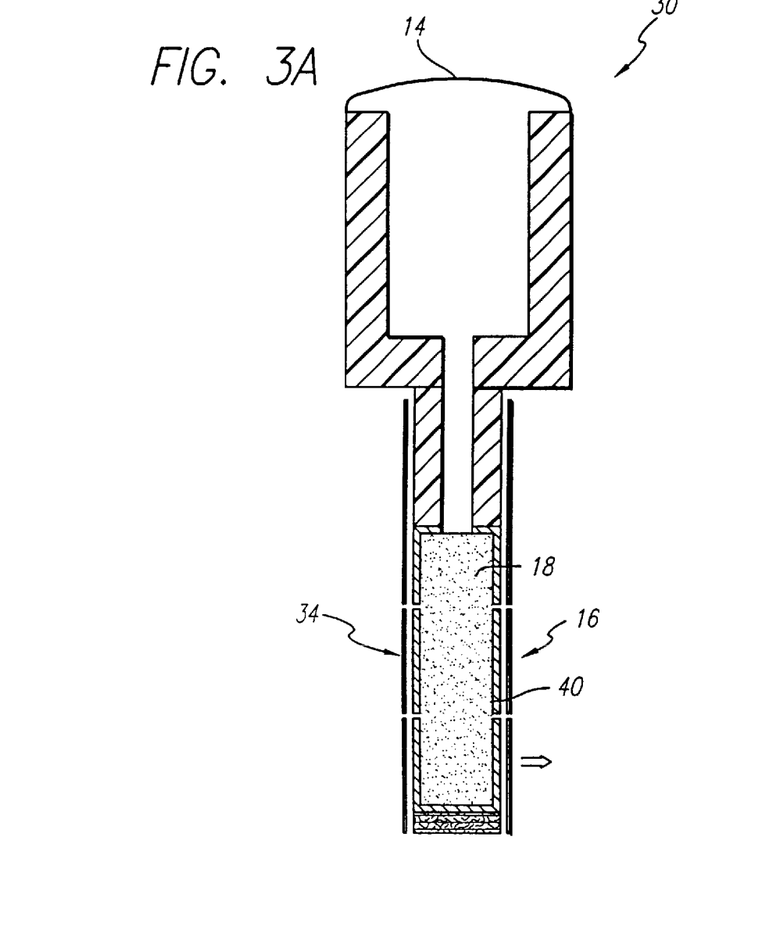
FIG. 3a is a side view of a horizontal gel loader with a permeable outlet area on both sides of the loader.
Figure 3B:
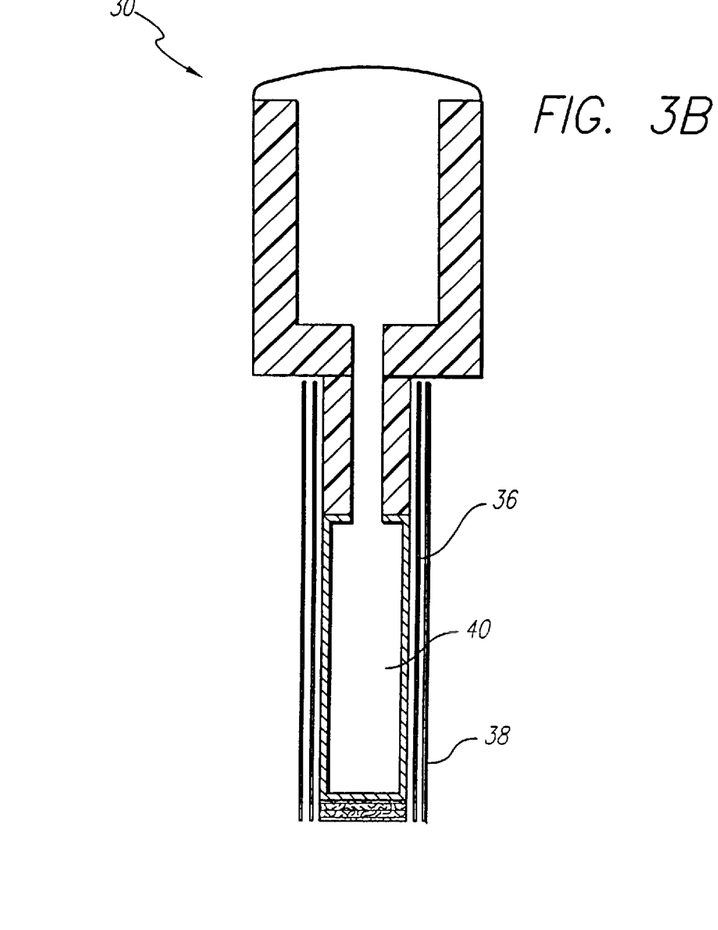
FIG. 3b shows a similar loader with an impermeable film on the exterior of the permeable outlet area.

Gels apparatuses are generally designed to hold gels in either a vertical orientation (typical for gels used for DNA sequencing and protein separations) or a horizontal orientation (typical for gels used restriction enzyme digests, Northern blots, and PCR analysis, including preparative and diagnostic uses). Loaders intended for use with a gel to be run in a vertical orientation, as in FIG. 1, will typically have the outlet or outlets located at the bottom edge of the loader. Loaders intended for use with a gel to be run in a horizontal orientation 30, as in FIG. 3a, will also have an inlet, a channel 18, and an outlet 16, which typically is covered by a porous or permeable membrane 36 (see FIG. 3b), along the side of the loader on which the electrophoresis is to take place. As noted below, in a horizontal gel loader, the side 34 away from that on which electrophoresis is to occur has to be porous to buffer or to have another means provided so that electric current from the electrophoretic apparatus can reach the sample and draw any charged molecules into the gel. The arrow to the right of the loader in FIG. 3a shows the direction of electrophoresis.

b). Thickness and Height

Gel apparatuses are also designed to hold gels of thicknesses appropriate for the purpose for which the gel is intended. For example, gels used for DNA sequencing are very thin, having a typical thickness of some 0.2 to 0.4 mm. In comparison, gels for separating proteins are somewhat thicker and gels for preparative PCR are comparatively quite thick, typically some 5 to 10 mm. Loaders for use in the invention are designed to fit into the apparatus holding the gel in place (or, in the case of gels to be poured with the loader in place, to fit into the gel forming apparatus). Accordingly, the thickness of the bottom portion of the loader will vary to fit into the gel apparatus with which it is to be used.

The thickness of the portion of the loader extending above the portion fitted into the gel forming or gel holding apparatus does not have a particular constraint on thickness. It may be thinner than the portion fitted to the gel apparatus, may be the same thickness, or may be thicker. In most embodiments, the portion of the loader will be the same thickness as or thicker than the portion fitted into the gel apparatus. In some preferred embodiments, the portion of the loader above the plates of a vertical gel holder (or the portion above the gel, for a horizontal gel) will be thicker than the portion fitted into the apparatus (or in the gel, for a horizontal gel). As shown in FIG. 4a, this permits the bore, or hollow, of the passage between the inlet and the outlet to be enlarged in capacity to define a reaction chamber, 40, in which a sample can be reacted with restriction enzymes, PCR reagents, or other reactants. In these embodiments, the reaction chamber 40 is thicker than the portion of the loader, 46, dimensioned to fit into the gel loading or holding apparatus.

As noted above, there is no particular constraint on the thickness of the portion of the loader extending above the gel apparatus for a vertical gel or above the gel, for a horizontal gel (in horizontal gels, the inlet area can be a separate piece fitted into the reaction chamber, as shown in FIG. 3, or the loader can be made as one unit). If a reaction chamber is desired in a loader, it need generally only be large enough to accommodate adequately the sample and reagents which may be necessary to perform any reactions or other operations to be performed in the loader. For example, if it is desired to perform PCR in the loader, the reaction chamber should be large enough to hold the volume of nucleotides, primers, enzymes, and template DNA required for that reaction to proceed, plus buffers for the following electrophoresis. Since the quantity of the sample needed for running even a preparative gel is not large (usually between about 10 to 200 $\mu$l for a standard PCR or restriction enzyme digest or for an RNA sample for a Northern blot, and 1 ml or less for a preparative sample), the volumes of the reactants and buffers needed to perform PCR, restriction digests, or other reactions in the well of a loader are correspondingly modest. Accordingly, the reaction chamber will typically not need to hold more than about 1 ml in total volume and can be designed to hold considerably less than that if the loader is not intended for use with respect to a preparative gel.

As shown in FIG. 3, in horizontal gel loaders, the reaction chamber 40 can be the whole passage, or a lower portion of the passage. FIG. 3 also illustrates that, in horizontal gel loaders, the outlet can be through a permeable wall (or side) of the loader 32.

Since larger thicknesses will use more material and presumably cost more, typically the upper potion of the loader will not be made larger or thicker than convenient for the intended uses. The thickness of the loader also has an upper limit based on the strength of the materials used and the stresses imposed on the thin section of the loader designed to fit into the gel apparatus. It is desirable that the thickness of the portion of the loader extending above the gel apparatus should not be so great as to cause the weight of the extending section to bend or to crack the loader at the point where it thins to fit into the gel apparatus. The thickness which could cause this to happen will depend both on the thinness of the portion of the loader fitting into the gel apparatus and on the strength of the particular material used to construct the loader, and can be calculated or, more typically, tested empirically. Such testing is routine for companies fabricating plasticware and the like. Variations on the dimensions of the reaction chamber and of the loader are exemplified in FIGS. 5a to 5p. FIG. 5r shows a front view of a loader comprising reaction chambers thicker than the portion of the gel.

Current electrophoresis apparatuses typically have a cover, often with integral leads for electrodes. The height of loaders intended for use with this equipment will generally be constrained by the space available between the top of the gel and the bottom of the cover to be placed over the electrophoresis apparatus. The height under the cover of the apparatus can be varied and the height of a loader can vary (as exemplified in FIGS. 5a to 5p) so long as it can be accommodated within the space available in the apparatus with which it is intended to be used.

c). Overall Dimensions; Multiple Chambers

Most commonly, electrophoresis and the like involves the running of numerous samples, and it is convenient to load as many samples in a single gel as can be accommodated by the equipment while keeping the lane corresponding to each sample adequately spaced from the lanes of the samples on either side to permit ready distinction of the samples.

Because of the widespread use of laboratory 96-well microtiter plates in all laboratory work, the width and length of these plates has become a de facto standard for much equipment designed in connection with automated sequencing of gels. (These plates are configured in a 12 well width, arrayed across the plate in a straight line, which is repeated in 8 rows along the length from "top to bottom," looking at the surface of the plate.) In a preferred embodiment of the invention, the loader has a width of or about the width of a 96-well microtiter plate (although it can have lateral extensions designed to engage equipment, such as the sides of a horizontal electrophoresis device) and the wells are separated at or about the same distance as are the wells on a microtiter plate. In an even more preferred embodiment, the loader has 12 chambers or wells, so that there is a well corresponding to each well in a single row of a microtiter plate, spaced as are the wells of a microtiter plate. Further, the loader preferably has a thickness which is one-eighth the length of a microtiter plate, so that eight loaders can be packaged together with overall dimensions (width and thickness, approximately 12×8 cm) of a 96-well microtiter plate. After the reactions are performed the eight individual loaders are separated and placed on gels for electrophoresis (in current practice, horizontal gels are often run with more than one comb, separated by an appropriate distance, to maximize use of the gel. Loaders of the invention can be substituted for the traditional combs and wells in such a setup).

An exemplar loader of such a design has a twelve reaction wells, with each well measuring 6 mm×7 mm×1.3 mm, and accommodating a reaction volume of over 50 µl, which is sufficient for most applications. The total width is of 11.5 cm, which will fit conveniently in commercially available vertical electrophoresis tanks, as well as horizontal electrophoresis devices, such as the Hybaid Midi electrophoresis tank Model HB-B2 (Hybaid Ltd., Ashford, Middlesex, England).

In a preferred embodiment, the outlet of a loader designed for use with a gel to be run in a vertical format defines a flat edge. This increases the chance that the sample enters the gel in a straight front, and increases the chance of having the macromolecules sort themselves in bands which are straight lines across the lane, which aids the analysis and interpretation of the results. It should be noted that the presence of the loader around the outlet can serve as insulation and resulted in band "smiling" (bands which define curves shaped like smiles rather than straight lines) when narrow outlets were tested. Band patterns returned to straight lines when the outlets were widened to 7 mm and the electrophoresis voltage was reduced to 40–80 volts for the first five minutes. Any desired width of the outlets can be easily tested to see if smiling will be induced by forming a loader with an outlet of the desired width, running a gel, and examining the resulting bands to determine if they are "smiling" or in straight lines.

As in FIGS. 1 and 2, the outlets 16 can be shaped, typically in a rectangle and often somewhat elongated, to increase the probability that the sample enters the gel in a straight line.

d). Spacing of Wells

The spacing of the inlets and the outlets need not necessarily be the same. In DNA sequencing, for example, it is desirable that the lanes be very close to one another so that a ready comparison can be made by eye of the lanes corresponding to the different nucleotides. Gels intended for DNA sequencing, for example, are currently loaded with a "shark's tooth" comb, which provides only the tip of the prongs as a spacing between the respective lanes. In the present invention, the inlets can be at the spacing for a 96-well microtiter plate (which helps facilitate automation), while the outlets are close together, to facilitate comparison by eye of the bands in the respective lanes.

In horizontal gels, the lanes are traditionally spaced further apart than are DNA sequencing gels. Because agarose tears easily when the comb is removed in conventional methods, the space between the prongs of the comb are spaced to ensure a portion of untorn agarose remains in place between the lanes. This spaces the lanes further apart than might otherwise be desired and results in fewer samples being run per gel. Because the loader of the invention stays in place during electrophoresis rather than being removed from the gel before it is run, use of the loader does not tear the agarose, and the lanes can be placed closer together, permitting more samples to be run in a single gel.

e). Electrodes

Traditionally, electrophoresis gels are run in tanks with a pair of electrodes to create a current through the gel. One electrode is usually positioned at the top of the apparatus and the second is at the bottom (or, in a horizontal gel, at the ends of the gel across its longer dimension). The present invention can be used in these typical configurations. The use of a single, top mounted electrode requires that the inlets at the top of the loader be open so that buffer can enter and provide a path for the electric current to travel through the sample and into the gel through the outlet. If desired, however, the loader can be designed with an electrode positioned in one or more of the wells, or a single electrode can be attached to the top of the loader, with connections to the interior of the individual wells. Optimal placement of the electrodes in the wells is readily determined by conducting parallel test runs to see which position provides the most complete electrophoresis of a known sample, and the most accurate compared to a traditional electrophoresis set-up.

The operation of the electrode will result in formation of hydrogen and oxygen. Therefore, during the conduct of electrophoresis, any cap on the passage should be removed or should be vented to permit the exit of the gases generated during the procedure. Further, the use of integral electrodes can result in the formation of charged radicals which can damage susceptible samples. This problem can be detected by running duplicate aliquots of sample, one on a device with an integral electrode and one on a device with a standard electrode setup. If the two samples do not show very similar electrophoretic patterns, the integral electrode can be used, and the initial voltage lowered to reduce this problem, or the electrophoresis of the sample can be switched to a standard electrode arrangement.

f). Common Inlets

In many applications, the same buffers, enzymes, or other reagents, may need to be added to each well, either in the course of a protocol such as electrophoresis or prior to electrophoresis. In one group of embodiments, as exemplified in FIG. 2, therefore, the loader has, in addition to the inlet 14 for each passage or well, one or more inlets 20 in fluid communication with more than one of the wells to provide an inlet common to each of the wells so connected. In loaders designed for PCR and restriction digests, the common inlet is preferably in fluid communication with all of the wells of the loader. The wells so connected can then be loaded with a common reagent at one time through the common inlet. In these embodiments, each passage therefore has two inlets. For example, in PCR, the reagents common to all the wells, such as Taq polymerase, can be delivered to each of the wells at the same time, rather than being added to each one individually. Conversely, the components of the reaction unique to a particular well, such as the forensic sample, gene of interest, or other template DNA on which the PCR is being conducted, are loaded into the appropriate well through the inlet specific to that respective well. Alternatively, it may be desirable to add the same template DNA to wells containing different PCR mixes, such as in a diagnostic application to detect if different genes or alleles are present in the DNA sample. A 12-well loader, for example, designed for PCR or other reactions involving reagents common to all of the wells on the loader will therefore have one inlet for each well plus a single inlet common to all, for a total of 13 inlets, as shown in FIG. 2.

Loaders designed for sequencing (which sometimes requires addition of the four nucleotides into four respective wells), by contrast, can have a common inlet serving each group of four wells, so that reagents common to each group of wells can be added through the common inlet. A typical 12-well loader designed for this purpose therefore will have 12 inlets serving the individual wells, and 3 common inlets, each of which is in fluid communication with a cluster of four wells, and will therefore have a total of 15 inlets. Loaders can also be designed for protocols requiring any particular number of wells which can fit comfortably on the dimensions of the loader, with any number of common inlets useful for that protocol. The use of such common inlets, of course, simplifies the automation of the process, and reduces the effort required by a technician if the wells are being loaded manually.

g). Preloaded Reagents

In another group of embodiments, loaders are provided which are already loaded in one or more wells with reagents needed for particular protocols. In this group of embodiments, the reagents will typically be dry reagents, which need only to be mixed with an appropriate amount of water to be ready for use. For example, pellets of dry reagents of components for performing PCR (minus, of course, the template DNA which will be the subject of the amplification) are commercially available. The pellets can be added to wells so that only the template DNA and water to dissolve the other reagents need be added to be ready to perform PCR. Liquid reagents can also be preloaded. Typically, loaders with preloaded reagents will have an appropriate cover of some sort on both the inlets and the outlets to prevent loss of the reagents prior to use.

h). Directing the Electric Current for Horizontal Gels

During electrophoresis of vertical gels, the inlets of the loader will typically be covered by running buffer, which provides a path for the electric current to flow through the sample and into the gel. In horizontal gels, the inlet portion of the loader will normally be above the running buffer during electrophoresis. Accordingly, it is necessary to provide a means for the electric current to flow through the sample.

This may be accomplished by any of a number of means. Conveniently, as shown in FIG. 3a, the loader has both the front 16 (the side facing into the direction the electrophoresis will occur) and back 34 (the side facing away from the direction of electrophoresis) of the portion of the loader in the gel made of a material permeable to the buffer and, hence, to the electric current. Since the electrodes in a horizontal gel are usually positioned at the ends of the apparatus, with the loader in between, this permits the current to flow through the loader and carry charged molecules from the sample into the gel for electrophoresis. Alternatively, the side of the loader 34 facing away from the area of the gel in which the electrophoresis is to occur can be of metal or of another material which conducts electricity. This permits the current to pass through the conductive material into the sample. Less preferably, material such as an impermeable cover can be removed from the back side of the loader to reveal a port, typically above the section containing the sample but within the area covered by the buffer, to permit the buffer (and, hence, the current) access to the sample.

In another embodiment, each well of the loader is provided with its own electrode, which may be connected to a common lead coming into the apparatus. In this embodiment, the electrode is positioned in the well in a manner providing current to the sample.

2. Barriers a). Internal Baffles or "Swan's Neck"

As exemplified in FIG. 4, in one set of embodiments, the loaders have one or more internal barriers to prevent nucleic acids, proteins, or other molecules of interest from exiting the outlet under normal gravity. In these embodiments, the passage or reaction chamber has a flange, baffle or other outward extension from the interior wall of the loader (hereafter all referred to as "baffles" for ease of reference) to provide a physical barrier to catch the molecules of interest before they can exit the passage or reaction chamber.

An immovable interior barrier, of course, cannot extend the entire width and thickness of the passage or reaction chamber, or there would be no way for the macromolecules to exit during electrophoresis. On the other hand, leaving some space open could allow undesired leakage or other loss of molecules of interest from the passage or reaction chamber. As shown in FIG. 4a, one preferred embodiment of an internal barrier therefore consists of two offset baffles or flanges 42 and 44, with the upper baffle 42 projecting downwardly on a slope from the internal wall of the loader, and the lower baffle 44 projecting upwardly on a slope from the opposing internal wall. Since the juncture (or "trough" 48) of the wall of the loader and the lower baffle is the lowest space afforded on the lower baffle, macromolecules 49 will be trapped and accumulate in the trough. They are, however, still in fluid communication with the inlet and the outlet of the well. Upon filling of the passage with a suitable buffer and the application of an electrical current, as occurs during electrophoresis (FIGS. 4c through 4e), the current draws charged macromolecules such as nucleic acids over the incline and into the gel (FIG. 4e), where they undergo electrophoresis separation. It should be noted that FIG. 4e shows only the top portion of a typical electrophoresis setup and that such setups are designed to draw macromolecules into the gel by a positive charge at the bottom of the electrophoresis setup (not shown).

b). Barriers at the Outlet i). Permeable Membranes

In place of, or in addition to, an internal, physical barrier, the loaders can have a barrier at the outlet. This barrier can take one of several forms. In a preferred group of embodiments, the barrier is a permeable membrane which permits electrophoresis of macromolecules through pores in the membrane. In this group of embodiments, the loader can therefore be loaded with samples and the samples later electrophoresed directly from the loader without having to remove the membrane prior to initiating electrophoresis.

A number of membranes suitable for use in the invention are commercially available. Polycarbonate membranes, in particular, have been tested and found to work well. Polycarbonate membranes are commercially available from several sources, including Millipore Corporation (Bedford, Mass.), which sells Isopore™ and Durapel™ membranes, and Corning Inc. Science Products Division (Acton, Mass.), which sells Nucleopore™ membranes. Membranes of a variety of pore sizes can be used in connection with the invention. Tests have shown, however, that pore sizes as large as 8.0 microns permit oozing of nucleic acids, while pore sizes smaller than 1.0 micron are easily blocked by debris. Accordingly, pore sizes about or larger than 1.0 microns and smaller than about 8.0 microns are preferred. More preferred are membranes with pore sizes of between about 1.0 and about 6.0. Even more preferred are membranes with pore sizes 1.0, 2.0, and 3.0 microns, with the 3.0 micron size being most preferred. Corning Nucleopore™ membranes in these sizes are particularly preferred. The Examples set forth information about the testing of different pore sizes.

Membranes made from materials other than polycarbonate can also be used in the permeable membranes. The materials should not have a high affinity for nucleic acids or proteins, and should be relatively inert. Methods for testing these properties is routine in the art, and can be conducted, for example, by electrophoresing two identical aliquots of a nucleic acid mixture, one through the permeable membrane being tested into a gel and the second in a gel loaded in a traditional manner, and comparing the resulting gels to see if there is a detectable reduction in the amount of nucleic acid evident in the gel run through the potential permeable membrane compared to the amount in the gel loaded in a traditional manner. In addition to the material itself, the membrane should have pore sizes which are of relatively consistent size, and which are between about 1.0 and about 6.0 microns, and preferably between about 1.0 and about 3.0 microns.

The permeable membrane can optionally be covered with an impermeable membrane or sleeve to avoid water loss in heating steps. Impermeable coverings for the permeable membrane are discussed in section c, below.

ii). Moveable Gates

In addition to permeable membranes, a number of other means to inhibit macromolecules from prematurely exiting the outlet can be used. One such means is a moveable gate. In this embodiment, the outlet of the loader is covered by an inpermeable material, such as glass, plastic, rubber or metal, closely enough so that there is not a significant loss of any of the sample, including water vapor, through the outlet. Preferably, the material should not have a high affinity for nucleic acids, proteins, or other molecules which might be subjected to electrophoresis.

Conveniently, the gate can slide along the side of the loader or along the bottom edge of the loader (depending on whether the outlet is positioned along the wall of the loader, as is typical for loaders used with horizontal gels, or along the bottom of the loader, as is typical for loaders used with vertical gels) to permit the sample or other contents to exit through the outlet. Preferably, the gate slides up. Alternatively, the gate can pivot or swivel around a pin or the like to uncover the outlet. Optionally, the gate can be operated by a wire or other means to open the gate once the loader is placed on the gel or the gel has set around the loader.

iii). Removable Covers

In yet another means to inhibit macromolecules from prematurely exiting the outlet of the loader, the outlet can be covered with a removable material. The removable material can be as simple as a tape which can be gently pulled off or up (so as to not disturb the surface of the gel) once the loader is positioned on the gel, or can be a cap designed to fit snugly on the outlet and removed just before electrophoresis. Preferably, if tape or other material is pulled off, it is pulled up rather than across the loader, so that any molecules of a sample which happen to adhere to the material are not inadvertently transferred to another portion of the gel.

The brief period that the outlet is uncovered before the loader is positioned on the gel will not generally result in loss in sample. Loaders designed for use with removable covers preferably have outlets sized so that the viscosity of the sample, and the effects of capillary action, retain the sample for at least a brief period. This is aided by the fact that samples prepared for electrophoresis are usually quite viscous due to the presence of proteins, enzymes, and other large molecules. It is of course desirable that the loader be positioned promptly after the material or cover is removed to avoid both loss of sample and to reduce the possibility of contamination of the sample. In loaders which have internal barriers, such as a "swan's neck" passage (as in FIG. 4a), the density of the sample itself generally hold it against the barrier until electrophoresis commences, whereupon the charged molecules in the sample are drawn over the barrier by the electric current.

For loaders with a multiplicity of passages, the cover can be a tape covering some or all of the outlets, or a series of caps on a connected strip, for example of plastic, so that all the caps for all the outlets can be easily and quickly removed. Additionally, regardless of whether the loader has one or a multiplicity of wells, it can be made with a twist off or snap off edge, which when twisted or snapped off places the well or wells in fluid connection with the exterior.

c). Removable Impermeable Material i). General

As noted above, the outlet of the loader can be covered with a permeable membrane permitting electrophoresis through the membrane. Performing some protocols, such as PCR, in the loader, can, however, require heating the loader. During heating, water vapor would be able to exit through the permeable membrane, resulting in an undesirable increase in the viscosity of the sample. To correct this problem, it is desirable that if the loader is to be heated (an optionally, at other times) to cover the permeable membrane with an impermeable material to reduce water loss through the permeable membrane, and to remove the impermeable covering prior to electrophoresis.

Films make especially convenient impermeable coverings. Plastic films, for example, can be made self-adhesive, and are commercially available. In addition to being impermeable, the films should be able to withstand repeated heating (to about 100° C.) and, if PCR is to be performed in the loader, should be able to transfer heat rapidly to and from the sample. Moreover, for applications in which storage of the sample in the loader is contemplated, both the film and the loader should be able to withstand storage at −20° C. or −80° C. Metallized films (which often are composed of a layer of plastic film bonded to a metal foil, usually aluminum) tend to have a high rate of heat transfer and are particularly preferred for that reason. A number of such films, bonded to different plastics, such as metal-polyethylene, metal-polypropylene, metal-polyethylene, and metal-polyester composites, are available. Some films are manufactured with such a strong adhesive that their removal can damage the underlying permeable membrane if they come into direct contact. This can be dealt with in any of several ways. First, one can select a film which is not as strongly adhesive, but is otherwise satisfactory. Second, if a highly adhesive film is to be used, it can be kept from direct contact with the permeable membrane. This can be done by, for example, using plastic, rubber, or another convenient, inert material, as a spacer to prevent direct contact of the adhesive impermeable film and the permeable film. Alternatively, the impermeable film can be bonded to the loader in a manner so as to provide a space between the permeable membrane and the impermeable film.

Impermeable films are widely available. A number of commercially available films have been tested and found suitable for use in the invention, as described in the Examples. Example 3 sets forth exemplar tests for determining the suitability of impermeable materials for use in the invention.

For some of the purposes to which horizontal gels are put, such as forensic identifications, it is desirable to retain and store a portion of a sample for later comparison or further analysis. Impermeable films are particularly convenient for this purpose. When the loader is placed in or against a horizontal gel, typically, the outlet will traverse a portion of the front of the loader. The film covering the top portion of the outlet can be removed, leaving the film covering the bottom portion of the outlet intact. The portion of the sample in the upper portion of the loader previously under the portion of the film that was removed is then able to undergo electrophoresis while the portion of the sample under the portion of the film which was not removed remains in the loader and can be stored for further use.

Another form of impermeable barrier would be a solid capable of dissolving upon exposure to an appropriate solvent. In this embodiment, the solvent can be within the gel, provided that neither it nor the dissolved barrier will interfere with the electrophoresis of the sample, or can be applied before the loader is inserted into the gel. Preferably, the barrier is dissolvable in an organic solvent, such as ethanol, rather than water, to avoid reaction with water in the reaction chamber or passage.

Alternatively, a removable metal or plastic sleeve can be fitted around the portion of the loader containing the outlets to serve as an impermeable covering. The sleeve can be designed to fit snugly against the loader by itself, or can be designed to form a moisture resistant seal against the loader by pressure from the equipment to be used to heat the loader, such as a PCR block.

3. Caps and Covers for the Loader

As noted above, some protocols which can be conducted in the loader require the use of heat, and the use of heat will result in the loss of water vapor through any opening. One such opening is the inlet used to load the sample in each passage. To close off the inlet, for example to prevent water loss during heating steps of protocols, the loader is optionally equipped with a cap or a cover for one or more of its inlets. The cover can be as simple as a plastic film or tape to seal the opening of the inlet. Alternatively, it can be a cap designed to fit the dimensions of the inlet. The cap can be of a pierceable rubber or other material, such as is used for covering vials of vaccines and other injectable drugs. Introducing samples and reagents through the covering reduces the potential for airborne and other contaminants to enter and is particularly useful with forensic samples. Further, introduction of reagents through such coverings is especially useful in automating the process, since it does not require that the equipment remove and replace the cap or other covering as an incident to loading.

In loaders intended for PCR and other protocols which require heating steps, the cap or other cover should fit tightly enough to withstand the increase in pressure which occurs due to the increase in vapor pressure in the interior of the loader as it is heated. Additionally, many current PCR machines are heated both at the bottom, to heat the sample, and at the top, to reduce condensation of water vapor on what would otherwise be the relatively cool top of the sample container. The top heater is normally maintained at about 94° to 100° C. The material employed for the cap or cover should be able to retain its integrity and sealing properties at those temperatures.

4. Body of the Loader

In preferred embodiments, the material composing the body of the loader can be labeled with a bar code or marked with a pen or a fluorescent ink pen. If the gel is then photographed with the loader in place, the photograph of the gel is then labeled and errors in labeling after the photograph has been developed avoided.

IV. USES OF THE LOADER

The invention may be used wherever molecules are being loaded into gels for electrophoresis. The invention is particularly useful in permitting the automation of electrophoresis in the sequencing and amplification of DNA, but its advantages of reducing handling and transfer of samples, of retaining samples in order, and in reducing exposure of laboratory workers to hazards, render it useful in many other contexts as well.

With respect to horizontal gels, for example, the loader increases the speed and reduces the chance for error and contamination in working with forensic samples, such as DNA obtained from crime scenes or persons suspected of being the source of bodily fluids or other evidence obtained during an investigation. Similarly, the loader is useful in medical diagnostic applications not only for the advantages just mentioned, but also in reducing the exposure of technicians to any biohazards which may be present in the samples. The invention will also prove useful in research for uncovering the genes associated with various phenotypes, including disease states, and with restriction enzyme digestions. Similarly, the invention can be used with respect to plant and agricultural applications to determine genes responsible for desired and for undesired plant traits, such as resistance to disease.

In addition to these study functions, the invention can also be used for preparative gels, not only for sequencing, but also for analytical and cloning applications. Finally, the invention can be used in connection with the electrophoresis of RNA in Northern blots and other procedures.

With respect to vertical gels, the invention will useful not only with respect to DNA sequencing, but also protein separation. Thus, the invention can be an important means to increase the speed and accuracy of immunoassays, Western blots, gel shift studies, and other methods by Which the presence or absence of proteins in a sample, or the changes in the proteins, are determined.

V. EQUIPMENT ADAPTED TO ACCEPT THE LOADER

1. Centrifuge

One piece of equipment readily adaptable for use with a loader of the invention is the centrifuge. Low speed centrifuges suitable for use in many protocols can be constructed by using a spindle designed to hold the loader at the top edge or along the upper portion, creating a centrifugal force to drive samples to the bottom of the loader. For low speed applications, the spindle may be driven manually, for example by a side mounted hand crank, although optionally, the centrifuge can be driven mechanically or electrically. If faster speeds are desired, or longer centrifugation is necessary, the centrifuge will usually be powered by an electric motor. Optionally, the centrifuge is further equipped with heating means, cooling means, or both, so that temperature cycling can take place while the samples are in the centrifuge.

2. PCR Block

PCR blocks can be adapted to accept loaders of the invention so that PCR can be performed in the loader. This permits the samples to be loaded once into the gel loader, and undergo PCR and then electrophoresis while only having to be subjected once to the stresses of micropipetting or being drawn into, and then expelled from fine gauge syringes.

EXAMPLES

The following examples are provided by way of illustration only and not by way of limitation. Those of skill in the art will readily recognize a variety of noncritical parameters that could be changed or modified to yield essentially similar results.

Example 1

Prototype Loader

This example demonstrates a prototype of a gel loader comb containing multiple chambers.

Flat strips were glued on either side of a standard shark's tooth sequencing comb. The flat strip on one side was shorter than that on the other so that the space between the shark's teeth nearest to the body of the comb could serve as a sample inlet on one side when the comb was in position on the gel. The base was sealed with 2% agarose, leaving a space above the agarose between each of the prongs of the comb (the "shark's teeth") and an open orifice (or inlet) for loading samples. A 'guillotine' (a vertical device for accelerating and then abruptly stopping the loader) was then constructed that held the loader. The loader was accelerated by use of two elastic bands on each end and was then stopped abruptly when it hit the solid support at the base of the 'guillotine'. This caused any liquid within the loader to be localized at the bottom of each chamber within the loader. The loader containing the sample liquid was then transferred to the top of a standard polyacrylamide sequencing gel (vertical format) with spacers suitably thick to allow the entry of the loader and the sample, and covered with a quantity of buffer to allow electrical contact between the sample and the electrode. Electrophoresis and subsequent staining of the gel then revealed transfer of the sample from the chambers through the agarose 'membrane' into the polyacrylamide gel.

Example 2

Electrophoresis through Permeable Membranes

This example sets forth the testing of permeable membranes to determine pore sizes and other criteria for use in the invention.

Corning Costar Nucleopore™ polycarbonate membranes (Corning Inc., Science Products Division, Acton, Mass.) were tested empirically to determine whether the membranes inhibited biochemical reactions such as PCR, or bound excessive amounts of DNA or proteins. For example, to determine whether the membrane bound excessive amounts of DNA, pieces of membrane 5 mm by 5 mm were cut and placed in a standard centrifuge tube, template DNA added, and PCR performed. A duplicate aliquot of template DNA was subjected to PCR in a tube identical except for the absence of the membrane, and the amount of PCR product obtained was compared by ethidium bromide staining. Comparable amounts of staining indicated that the membrane was not binding undesirable amounts of DNA or otherwise inhibiting the reaction.

The membranes were then tested to determine the size requirements, if any, to allow a sample (such as a nucleic acid mixture or a protein) to move from the sample chamber of the loader to a gel under electrophoresis. All the polycarbonate membranes tested were 6–13 microns in thickness; the pore sizes tested were (in microns):

0.015, 0.03, 0.05, 0.08, 0.1, 0.2, 0.4, 0.6, 0.8, 1.0, 2.0, 3.0, 8.0 and 10.0.

Only the 0.015 micron pore size restricted the electrophoresis of DNA; all the pore sizes below 1.0 micron, however, became blocked easily, while offering no substantial advantages compared with the larger pore sizes. The largest pore sizes, 8.0 and 10.0 microns, permitted a slight amount of the DNA to ooze through the membrane when in contact with the buffer in the gel electrophoresis tank. If the amount of sample is adequate, some diffuseness in the resulting bands is acceptable, or the electrophoresis is to be run immediately, then this oozing can be acceptable. The 1.0, 2.0, and 3.0 micron pore sizes, however, were sufficiently small that surface tension prevented oozing, but were large enough to permit electrophoresis without being easily blocked.

The polycarbonate membranes were easily sealed onto the plastic of the gel loader using a strong, fast-setting cyanoacrylate glue (Loctite, Hartford, Conn.). The Coming Costar Nucleopore™ membranes tested had a PYP covering to aid wetting. Removal of the PVP by wetting with 70% ethanol resulted in better performance. Nucleopore membranes without PVP are also commercially available from Corning Costar.

Other membranes were also tested for suitability, employing two major criteria: whether they tended to inhibit PCR and whether they were porous to DNA under electrophoretic conditions. The results are shown in the table below. The column titled "PCR" indicates whether the film was judged suitable ("+") or not suitable ("−") for PCR, and the column titled "Electro." indicating whether the film was judged suitable or not suitable for electrophoresis. Films judged not suitable by one test did not necessarily have the second test performed. Liquid tended to spread from the chamber sideways through one thick, absorbent membrane tested when the loader was left standing. This membrane was deemed not suitable on this basis. Films that were judged satisfactory for both electrophoresis and PCR are shown in bold.

| Manu-facurer mm | Name | Material | PCR | Elec-tro. | Thick-ness (mm) | Pore |
|---|---|---|---|---|---|---|
| Millipore | Durapore ® | PVDF | – | | | |
| | Fluoropore ™ | PTFE/PE | + | – | | |
| | Isopore ™ | Poly-carbonate | + | + | 175 | 0.2 |
| | Durapel ™ | PVDF ("Super Hydro-phobic" ("SHP")) | + | + | 10 100 | 0.05 0.1 |
| | Millex ®-HA | Cellulose ester/PVC | – | | | |
| | Millex ®-GS | Cellulose ester/PVC | – | | | |
| | PVCO | PVC | + | – | | 0.8 |
| | VSWP | Cellulose ester | – | | | |
| Sartorius | N11306 | Nitro-celluclose | – | | | |
| | SM13229 | Cellulose TriAcetate | + | – | | |
| Amersham | Hybond ® N+ | Nylon | – | + | | |
| Boehr-inger | Hybridization | Nylon | + | – | | |
| Corning | Nucleopore ™ | Poly-carbonate | + | + | 10 | |
| Amicon | Centricon ®-10 | YM | – | | | |
| | Centricon ®-30 | YM | – | | | |

Example 3

Testing of Impermeable Membranes

This example concerns the testing of impermeable membranes to reduce water loss through a permeable membrane during heating or storage of the loader.

The permeable membrane tested in the previous example is permeable to water vapor. Some loss of water could occur during some procedures for handling nucleic acid or protein samples. In particular, if PCR is conducted in the loader, the heating of the sample would cause substantial loss of water if only a permeable membrane surrounds or forms the bottom portion of the loader.

To address this concern, testing was conducted in which the permeable membrane was covered with an impermeable membrane to see if the loader could be made with such a membrane in place for PCR or other procedures and then removed prior to initiating electrophoresis. Tests for impermeability were conducted by covering a test loader with a permeable membrane and then with the subject impermeable membrane, loading the chamber with 50 µl of water, and capping the inlet. The loader was weighed, and then heated to 94° C. for 10 minutes. The loader was then weighed again to determine if there was any loss of water vapor. Loss of water vapor, of course, indicates that the material is too permeable to serve as an impermeable cover.

Another test was whether the material adhered too strongly to the permeable membrane. The test loader was covered with permeable membrane and then with the candidate impermeable cover. The impermeable cover was then carefully removed and the process observed to see if the cover could be removed without tearing the permeable membrane. If the permeable membrane remained intact, it was then examined to determine if adhesive from the cover entered the pores of the permeable membrane such that it would block electrophoresis of samples. This determination was made by running an aliquot of a nucleic acid sample through the permeable membrane into the gel, staining the gel with ethidium bromide, and comparing the amount of DNA seen in the gel against that seen in a gel run of a duplicate aliquot of sample run through a loader with a fresh permeable membrane of the same material as that used in the test loader.

A further criterion for use in connection with protocols requiring heating is the rapidity with which heat is transferred to and from the sample. This rapid transfer is particularly important in PCR protocols. In a preferred group of embodiments, the impermeable cover is a metal film or a metallicised film (a plastic film combined with a metal foil), due to their rapid transfer of heat to and from the samples.

A series of commercially available, self adhesive, metallicised film were tested. Metallicised films were chosen because they conduct heat well and were therefore suitable for use with the rapid temperature changes needed to perform PCR. Moreover, they are attractive, impermeable to liquid, and easy to apply. The only significant problem with these films is that some of them tended to adhere too well; making it somewhat difficult to remove after PCR without ripping the underlying porous membrane.

Five self adhesive metallicised films, commercially available from Avery Dennison ("AD," Maidenhead, Berkshire, England), and one from Raflatac (Raflatac, Ltd., Eastfield, North Yorkshire, UK), were tested for their ability to be removed from a loader after cycling to 94° or to 100° C. The films tested, and their response after being cycled once to 100° C. (left column) or five times to 94° C. (right column), were as follows:

| Raflatac ® (R2RP3728) | Poor | OK |
|---|---|---|
| AD FasCal ® Embossing Gold 750 | Very good | Very good |
| AD FasCal ® 71 | Very good | Good |
| AD FasCal ® Satin Chrome 711 | OK | Poor |
| AD FasCal ® Brushed Chrome 772 | Good | Good |
| AD Transparent | Very good | Very good |

All the films were found (by pulling a length of the film between the hands) to be more than strong enough for use in the invention. Testing with these films established that they reduced water loss (as measured by weighing the loaders before and after heating) to acceptable levels.

Loader chambers were also successfully sealed with Corning Costar "Pressure sensitive plate sealer" (Cat. No. 3095), an adhesive backed, clear plastic film. Once positioned, the film could be removed from the underlying polycarbonate membrane without tearing or damaging it. This allowed a plasmid digestion to be conducted in the loader and, after removal of the film, subsequent electrophoresis of the loader contents into a gel.

Example 4

Cycle Sequencing of DNA with the Gel Loader

This example sets forth typical cycle sequencing using Taq DyeDeoxy (part of the Prism® Ready Reaction DyeDeoxy Terminator Cycle Sequencing Kit, Applied Biosystems, Calif.). Cycle sequencing is a well known technique method of sequencing DNA using Taq polymerase to increase the amount of sequencing product.
1. Add 5 µl of mineral oil.
2. Spin at 3K for 5 sec.
3. Load loaders with primer, M13 DNA, 4×fluor ddNTP's, dNTP's, Taq polymerase.

4. Spin at 3K for 5 sec.
5. Set thermal cycling parameters and run program.
6. Add 15 µl of 1×TBE electrophoresis buffer.
7. Spin at 3K for 5 sec (this displaces the mineral oil).
8. Remove loaders from apparatus, slide between glass plates of premade sequencing gel in buffer chamber (or pour acrylamide in the presence of the loaders).
9. Run gel.
10. Membrane will retain unincorporated fluorescent ddNTP's, DNA will electrophorese into gel.
11. Discard used loaders, process gel normally.

Example 5

Exemplar Sequenase Sequencing

This example shows typical sequenase sequencing using the invention.

1. For each template, add labeling mix with fluorescent or isotope labeled nucleotide and Sequenase to four chambers of a loader.
2. Anneal primer with template DNA in a 0.5 ml tube.
3. Split annealed DNA into 4 passages of a loader containing labeling mix.
4. Spin at 3K for 5 sec to start labeling reaction.
5. Incubate at room temperature for 4 minutes.
6. Add appropriate ddNTP to each labeling reaction.
7. Spin at 3K for 5 sec to start termination reactions.
8. Incubate at 37° C. for 5 mins.
9. Follow steps 8–11 of previous example.

Example 6

Exemplar PCR Protocol

This example sets forth an exemplar protocol in which PCR is performed directly in the gel loaders ("combs"). This protocol uses a layer of mineral oil, rather than a cap, to contain water vapor during the heating portions of the PCR cycle.

1. Add 5 µl of mineral oil.
2. Spin at 3K for 5 sec.
3. Load combs with primer, template DNA, buffer, dNTP's, Taq polymerase.
4. Spin at 3K for 5 sec.
5. Set thermal cycling parameters and run program in apparatus.
6. Remove combs from apparatus and place them against edge of horizontal agarose gel.
7. Run gel.
8. Discard used combs, process gel normally.

Example 7

Exemplar Restriction Digest Protocol

This example sets forth an exemplar protocol in which a restriction digest is performed directly in the gel loaders ("combs").

1. Add 5 µl of mineral oil (optional).
2. Spin at 3K for 5 sec.
3. Load combs with DNA, buffer, restriction enzyme.
4. Spin at 3K for 5 sec.
5. Set incubation parameters (e.g., 37° C.×30 minutes) and run program.
6. Remove combs and place them against the edge of a horizontal agarose gel.
7. Run gel.
8. Discard used combs, process gel normally.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. An "in situ" loader for electrophoretic gels, the loader comprising: a body, including at least one passage defining a space therein, the passage including an inlet and an outlet having a thickness of 10 mm or less, wherein the inlet and the outlet are spaced along the passage in fluid communication, wherein at least a part of the loader is of a dimension which permits insertion of that part of the loader into a gel holding portion of an electrophoresis apparatus, and comprising a non-absorbent barrier, which barrier is located inside the passage between the inlet and the outlet, to prevent any macromolecules in the passage from flowing to the outlet under normal gravity.

2. A loader of claim 1, wherein the space defined by said passage defines a reaction chamber.

3. A loader of claim 1, containing a plurality of passages.

4. A loader of claim 1, having at least one outlet defining a flat edge.

5. A loader of claim 1, wherein the loader is made of a material which has a low affinity for binding protein and for binding nucleic acids.

6. A loader of claim 1, wherein the loader has a top edge and the inlet is located in, at or along the top edge.

7. A loader of claim 1, wherein the barrier is a permeable membrane.

8. A loader of claim 7, wherein the permeable membrane is covered, externally to the passage, with a removable impermeable material.

9. A loader of claim 8, wherein the removable impermeable material is bonded to the loader.

10. A loader of claim 8 wherein the removable impermeable material is thermally bonded to the loader.

11. The loader of claim 8, wherein the removable impermeable material is selected from the group of a metal foil, a metallized film, and a plastic film.

12. The loader of claim 8, wherein the removable impermeable material is selected from the group of a metal sleeve and a plastic sleeve.

13. A loader of claim 7, wherein the permeable barrier is selected from the group consisting of polycarbonate membrane and PVDF(SHP).

14. A loader of claim 13, wherein the polycarbonate membrane has one or more pores between about 1 micron and about 6 microns in size.

15. A loader of claim 1, wherein the barrier is a baffle.

16. A loader of claim 1, wherein the barrier is movable.

17. A loader of claim 1, wherein the barrier is removable.

18. A loader of claim 1, wherein the passage in the top portion of the reaction chamber has a front side and a back side, defining a space between the front and back sides, wherein the bottom portion of the loader has a front side and a back side, defining a space between the front and the back sides, and wherein the space between the front and back sides of the passage in the top portion of the loader is larger than the space between the front and back sides of the part of the bottom portion of the loader which can be inserted into the gel electrophoresis apparatus, and comprising a non-absorbent barrier, which barrier is located inside the passage between the inlet and the outlet, to prevent any macromolecules in the passage from flowing to the outlet under normal gravity.

19. A loader of claim 1, wherein the loader is able to withstand G forces in excess of 1 without loss through the outlet of a liquid in the passage.

20. A loader of claim 1, wherein the passage comprises an electrode.

21. A loader of claim 1, wherein the passage comprises a reagent.

22. An "in situ" loader for electrophoretic gels, the loader comprising: a body, including at least one passage defining a space therein, the passage including an inlet and an outlet wherein the inlet and the outlet are spaced along the passage in fluid communication, wherein at least a part of the loader is of a dimension which permits insertion of that part of the loader into a gel holding portion of an electrophoresis apparatus wherein the loader has a top edge and the inlet is located below the top edge.

23. A loader of claim 22, wherein the inlet is angled upward.

24. An "in situ" loader for electrophoretic gels, the loader comprising: a body, including at least one passage defining a space therein, the passage including an inlet and an outlet wherein the inlet and the outlet are spaced along the passage in fluid communication, wherein at least a part of the loader is of a dimension which permits insertion of that part of the loader into a gel holding portion of an electrophoresis apparatus, wherein the loader comprises a metal film, a metal foil, or a metallized plastic, which metal film, metal foil or metallized plastic transfers heat to and from any contents of the loader at a rate suitable for conducting polymerase chain reaction.

25. An "in situ" loader for electrophoretic gels, the loader comprising: a body, including at least one passage defining a space therein, the passage including an inlet and an outlet wherein the inlet and the outlet are spaced along the passage in fluid communication, wherein at least a part of the loader is of a dimension which permits insertion of that part of the loader into a gel holding portion of an electrophoresis apparatus, and comprising at least two outlets and at least two inlets, wherein the outlets are spaced more closely together than are the inlets.

26. An "in situ" loader for electrophoretic gels, the loader comprising: a body, including at least one passage defining a space therein, the passage including an inlet and an outlet wherein the inlet and the outlet are spaced along the passage in fluid communication, wherein at least a part of the loader is of a dimension which permits insertion of that part of the loader into a gel holding portion of an electrophoresis apparatus, comprising at least two passages with individual first inlets, and further comprising a second inlet in fluid communication with at least two of the passages.

27. An "in situ" loader for electrophoretic gels, the loader comprising: a body, including at least one passage defining a space therein, the passage including an inlet and an outlet wherein the inlet and the outlet are spaced along the passage in fluid communication, wherein at least a part of the loader is of a dimension which permits insertion of that part of the loader into a gel holding portion of an electrophoresis apparatus, and further comprising a front side and a back side, wherein the back side is made of metal or another material conductive of electricity.

28. A system comprising of (i) an "in situ" loader for electrophoretic gels, the loader comprising: a body, including at least one passage defined therein, the passage including an inlet and an outlet wherein the inlet and the outlet are spaced along the passage in fluid communication, and further wherein at least a part of the loader is of a dimension which permits insertion of that part of the loader into a gel holding portion of an electrophoresis apparatus, (ii) a gel, and (iii) a non-absorbent barrier, which barrier is located in a position selected from the group consisting of inside the passage between the inlet and the outlet, to prevent any macromolecules in the passage from flowing to the outlet under normal gravity, and at the outlet.

29. A method for separating macromolecules electrophoretically using an electrophoretic gel, wherein said macromolecules are loaded into a loader having an inlet in fluid communication with a hollow passage in fluid connection with an outlet and comprising a non-absorbent barrier, which barrier is in a position selected from the group consisting of located inside the passage between the inlet and the outlet, to prevent any macromolecules in the passage from flowing to the outlet under normal gravity, and at the outlet said macromolecules being drawn through said outlet into a gel upon application of an electric current.

30. A kit comprising (i) an "in situ" loader for electrophoretic gels, the loader comprising: a body, including at least one passage defined therein, the passage including an inlet and an outlet wherein the inlet and the outlet are spaced along the passage in fluid communication, and further wherein at least a part of the loader is of a dimension which permits insertion of that part of the loader into a gel holding portion of an electrophoresis apparatus and further comprising a non-absorbent barrier, which barrier is located in a position selected from the group consisting of (a) inside the passage between the inlet and the outlet, to prevent any macromolecules in the passage from flowing to the outlet under normal gravity, and (b) at the outlet and (ii) a gel electrophoresis apparatus.

31. An "in situ" loader for electrophoretic gels, the loader comprising: a body, including at least one passage defined therein, the passage including an inlet and an outlet having a thickness of 10 mm or less, wherein the inlet and the outlet are spaced along the passage in fluid communication, and further wherein at least a part of the loader is of a dimension which permits insertion of that part of the loader into a gel holding portion of an electrophoresis apparatus, further comprising a barrier at the outlet, wherein the barrier is a non-absorbent permeable membrane.

32. A loader of claim 31, wherein the permeable membrane is selected from the group consisting of polycarbonate and PVDF(SHP).

33. A loader of claim 31, wherein the permeable membrane is covered, externally to the passage, with a removable impermeable material.

34. The loader of claim 33, wherein the removable impermeable material is selected from the group consisting of a metal sleeve and a plastic sleeve.

35. A loader of claim 33, wherein the removable impermeable material is bonded to the loader.

36. A loader of claim 33, wherein the removable impermeable material is thermally bonded to the loader.

37. The loader of claim 33, wherein the removable impermeable material is selected from the group consisting of a metal foil, a metallized film, and a plastic film.

38. An "in situ" loader for electrophoretic gels, the loader comprising: a body, including at least one passage defined therein, the passage including an inlet and an outlet wherein the inlet and the outlet are spaced along the passage in fluid communication, and further wherein at least a part of the loader is of a dimension which permits insertion of that part of the loader into a gel holding portion of an electrophoresis apparatus, further comprising a means for inhibiting macromolecules from prematurely exiting the outlet which means is selected from the group consisting of a moveable gate and a removable cover.

* * * * *